(12) United States Patent
Marshall et al.

(10) Patent No.: US 8,211,133 B2
(45) Date of Patent: Jul. 3, 2012

(54) LANCETS

(75) Inventors: Jeremy Marshall, Jericho (GB); David Danvers Crossman, Christmas Common (GB); Ernest John Mumford, Witney (GB)

(73) Assignee: Owen Mumford Limited, Oxford (GB)

( * ) Notice: Subject to any disclaimer, the term of this patent is extended or adjusted under 35 U.S.C. 154(b) by 443 days.

(21) Appl. No.: 10/503,633

(22) PCT Filed: Feb. 5, 2003

(86) PCT No.: PCT/GB03/00473
§ 371 (c)(1),
(2), (4) Date: Feb. 17, 2005

(87) PCT Pub. No.: WO03/066140
PCT Pub. Date: Aug. 14, 2003

(65) Prior Publication Data
US 2005/0119681 A1   Jun. 2, 2005

(30) Foreign Application Priority Data

Feb. 5, 2002   (GB) .................................. 0202603.7

(51) Int. Cl.
*A61B 17/14* (2006.01)
(52) U.S. Cl. ...................................................... 606/181
(58) Field of Classification Search .................. 606/181, 606/182, 167, 183; 600/583; 604/264, 272
See application file for complete search history.

(56) References Cited

U.S. PATENT DOCUMENTS

| | | | | | |
|---|---|---|---|---|---|
| 3,358,689 | A | * | 12/1967 | Higgins | 606/181 |
| 4,203,446 | A | * | 5/1980 | Hofert et al. | 606/182 |
| 4,452,243 | A | * | 6/1984 | Leopoldi et al. | 606/182 |
| 4,545,376 | A | * | 10/1985 | Beiter | 606/181 |
| 4,580,564 | A | * | 4/1986 | Andersen | 606/172 |
| 4,889,117 | A | * | 12/1989 | Stevens | 606/181 |
| 4,976,724 | A | * | 12/1990 | Nieto et al. | 606/181 |
| 5,151,231 | A | * | 9/1992 | Lambert et al. | 264/108 |
| 5,318,584 | A | * | 6/1994 | Lange et al. | 606/182 |
| 5,324,303 | A | * | 6/1994 | Strong et al. | 606/181 |
| 5,395,387 | A | * | 3/1995 | Burns | 606/181 |
| 5,423,847 | A | * | 6/1995 | Strong et al. | 606/182 |
| 5,456,875 | A |   | 10/1995 | Lambert | |
| 5,707,384 | A | * | 1/1998 | Kim | 606/181 |
| 5,871,494 | A | * | 2/1999 | Simons et al. | 606/181 |
| 5,964,731 | A | * | 10/1999 | Kovelman | 604/110 |
| 2003/0212423 | A1 | * | 11/2003 | Pugh et al. | 606/181 |

FOREIGN PATENT DOCUMENTS

| | | |
|---|---|---|
| EP | 0 017 999 | 10/1980 |
| EP | 0 174 011 | 3/1986 |
| EP | 0 447 726 | 9/1991 |
| FR | 2 595 237 | 9/1987 |
| GB | 2 352 403 | 1/2001 |

* cited by examiner

*Primary Examiner* — S. Thomas Hughes
*Assistant Examiner* — Jonathan W Miles
(74) *Attorney, Agent, or Firm* — Young & Thompson

(57) ABSTRACT

A lancet has a generally tubular body (1). A hollow insert (4) with a closed end plugs one end of the body (1), and it has a co-axial projection (5) forming a sharp tip proud of that end of the body. The body (1) and insert (4) are simultaneously formed by twin shot moulding, the body being of polyethylene and the insert being of a liquid crystal polymer which will create a sharp tip of adequate strength.

16 Claims, 1 Drawing Sheet

LANCETS

This is a 371 National Stage application of International application no. PCT/GB03/00473, filed Feb. 5, 2003, which claims priority to Great Britain application no. 0202603.7, filed Feb. 5, 2002. The entire contents of the above-referenced applications are hereby incorporated by reference in their entirety.

BACKGROUND OF THE INVENTION

This invention relates to lancets for skin prickers, used to draw a drop of blood for analysis.

The conventional construction of such a lancet is a steel needle encased almost entirely in an elongate plastics body but with its sharp tip projecting from one end. The plastics body eases handling and can be shaped to be guided by a compatible firing device and to locate one end of a spring which shoots the lancet forwards when released. It is also quite usual to have the needle tip encased in a twist-off cap integrally moulded with the plastics body. This keeps the tip safe and clean until immediately before use.

One problem with steel needles is that they are generally straight cylindrical bodies, apart from their tips, and they may be siliconised. Therefore the plastics of the body can have very little frictional grip on the needle that it encases, and it is not unknown for the needle to be shifted forwards relative to the body when the cap is twisted and pulled. This results in too deep a prick when the lancet is fired.

The manufacture of such a lancet necessarily involves more than one step. The steel needle has to be made first, and this in itself means taking a blank and then grinding or otherwise sharpening one end to create the tip. Then the needle is located in a mould, and finally is encased in the plastics body. It would clearly be advantageous to reduce the number of operations and form the needle tip with the body. However, an all-steel lancet would be far too extravagant, if nothing else since lancets are disposable, single use items, while simply moulding the body to have a tip at one end of the same material as the plastics body will not produce a sharp enough point if the usual plastics (polyethylene) is employed.

It is the aim of this invention to overcome, at least in part, these drawbacks.

SUMMARY OF THE INVENTION

According to the present invention there is provided a lancet for skin pricking, the lancet comprising an elongate plastics body with a plastics insert affixed at one end providing a sharp tip projecting from that end, the plastics material of the insert being a liquid crystal polymer.

Such a liquid crystal polymer, when melted, has extremely low viscosity and can-flow almost like water. It can therefore penetrate fully into the part of a mould cavity which will form the needle tip. Moreover its strength when set in the direction of flow is very high. Therefore the insert emerges from the mould with the tip sharp and ready for use.

Liquid crystal polymers are expensive, and so the body of the lancet will be of less costly material and polyethylene can continue to be used.

The body and the insert can be formed together in a single process by twin-shot moulding.

In the preferred form the body is generally tubular, the insert plugging one end. This enables the spring of a firing device to enter the other, open end of the body and to act directly on the insert, the body then serving primarily as guide member. Because the spring would not then act on the rear end of the body, this could enable the firing device to be more compact than existing ones.

A further advantage of the all-plastics construction is that such lancets will be easier to dispose of completely by incineration: there will be no steel needles to melt down or burn away.

While many firing devices automatically retract lancets to make them safe after use, this all-plastics lancet can quite easily be made safer to some degree if the tip is exposed. By pressing the tip at an angle against a hard surface the extremity can be broken off, leaving a blunted stump.

For a better understanding of the invention one embodiment will now be described, by way of example, with reference to the accompanying drawing, in which:

DETAILED DESCRIPTION OF THE INVENTION

Figure 1:
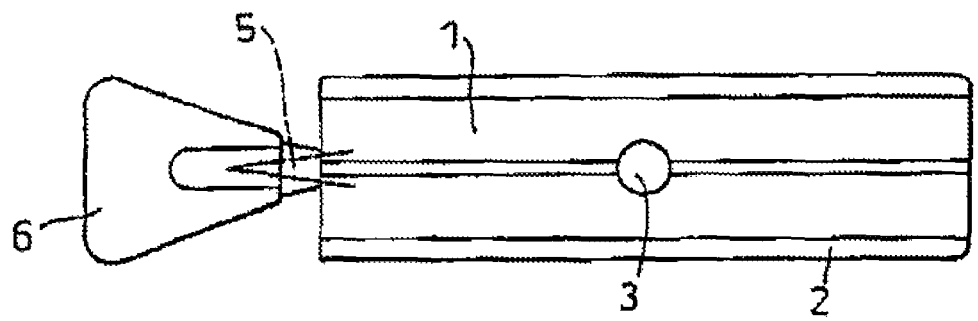
FIG. 1 is a side view of an all-plastics lancet of the invention.
Figure 2:
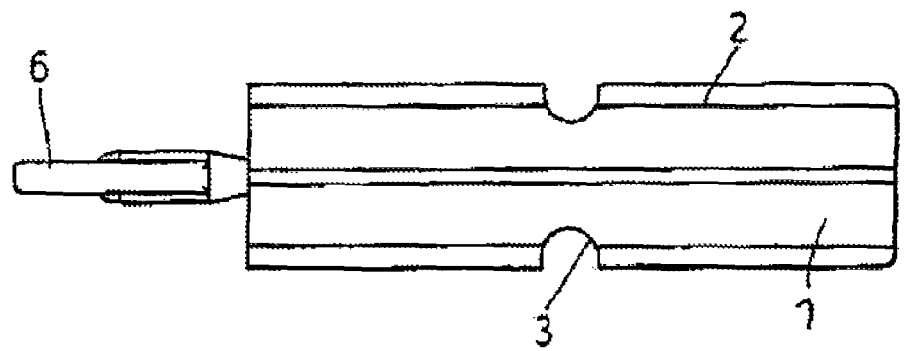
FIG. 2 is a side view at 90° to that of FIG. 1.
Figure 3:
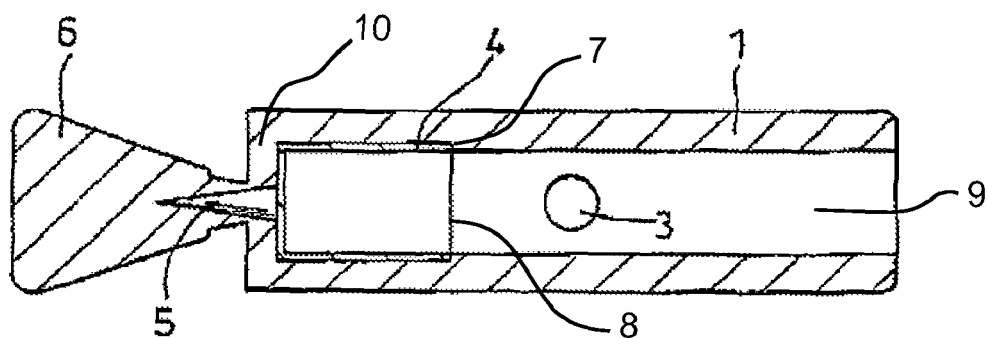
FIG. 3 is a cross-section through the lancet shown in FIG. 1.

The lancet has a generally tubular body 1 with four evenly spaced external longitudinal fins 2. Two opposed ones are interrupted at their mid-length by apertures 3 through the body 1, left as part of the moulding process.

A hollow insert 4 with a closed end plugs one end of the body 1, and it has a co-axial projection 5 forming an integral sharp tip proud of that end of the body. A cylindrical rear portion of insert 4 includes a rear-facing edge 8 abutting an interior shoulder 7 within the body 1. The forward end of the body 1 is closed by an end wall 10. The insert 4 and the body 1 together can define a contiguous or uninterrupted tubular passage 9.

The insert 4 is moulded first as a monolithic structure, then the body 1 is moulded over the insert 4 during a twin-shot moulding process, forming a twist-off cap 6 which provides a sterile shield surrounding and protecting the needle tip 5. The body is formed from a low cost relatively soft material such as polyethylene, whilst the insert is formed from a liquid crystal polymer.

The invention claimed is:

1. A lancet for skin pricking, comprising:
an elongate tubular plastic body of a first plastic material, the body having a forward end and a rearward end, and an interior surface defining a first tubular region; and
a hollow plastic insert of a second plastic material, the first plastic material being different from the second plastic material,
the plastic insert being molded to form a monolithic structure comprising a second tubular region that defines a hollow cylindrical rear portion, a closed forward end, and an integral sharp tip at the closed forward end,
the plastic insert located within the body and with the integral sharp tip projecting through said forward end of the body,
the body being molded over the insert such that:
the forward end of the body is closed by an end wall, with the sharp tip of said insert projecting from a forward surface of the end wall, and a rear surface of the end wall abuts the closed forward end of the insert, blocking forward movement of the insert relative to the body; and the body forms an interior shoulder within the first tubular region which abuts the cylindrical rear portion of the insert, blocking rearward movement of the insert relative to the body, thereby affixing the insert within the body, wherein, the plastic insert is immovable relative to the body, the second plastic material forming the plastic insert is a liquid crystal polymer, and the first tubular region and the second tubular region together define a tubular passage closed at said forward end.

2. The lancet according to claim 1, wherein the first plastic material comprises polyethylene.

3. The lancet according to claim 1, wherein the body and the plastics insert have been formed together in a single operation by twin-shot moulding.

4. The lancet according to claim 1, wherein the body further comprises external fins extending longitudinally on an external surface of the body.

5. The lancet according to claim 1, further comprising a twist-off cap integral with the body and covering the sharp tip.

6. The lancet according to claim 1, wherein the first tubular region and the second tubular region together define a contiguous tubular passage.

7. The lancet according to claim 1, wherein the first tubular region and the second tubular region together define an uninterrupted tubular passage.

8. A lancet for skin pricking, comprising:

an elongate tubular plastic body, the body having a forward end and a rearward end, and an interior surface defining a first tubular region; and a hollow liquid crystal polymer insert, the polymer insert being a monolithic structure comprising a second tubular region and a closed forward end providing an integral sharp tip, the insert being located within the body, with an outer surface of the insert contacting an inner surface of the forward end of the body, blocking forward movement of the insert relative to the body, and with the integral sharp tip projecting through said forward end of the body, and an outer surface of a rearward end of the insert contacting an interior shoulder of the body, blocking rearward movement of the insert relative to the body, wherein the first tubular region and the second tubular region together define a tubular passage closed at said forward end, and the insert is immovable relative to the body.

9. The lancet according to claim 8, wherein the body is formed from polyethylene.

10. The lancet according to claim 8, wherein the body further comprises external fins extending longitudinally on an exterior surface of the body.

11. The lancet according to claim 8, further comprising a twist-off cap integral with the body and covering the sharp tip.

12. The lancet according to claim 8, wherein said second tubular region defines a hollow cylindrical rear portion of said insert.

13. The lancet according to claim 12, wherein said hollow cylindrical rear portion is closed at a forward end by a planar end wall, and the end wall comprises a forward surface through which projects said sharp tip.

14. The lancet according to claim 12, wherein, said body comprises an interior shoulder within said first tubular region, and said cylindrical rear portion of said insert comprises a rear-facing edge abutting the shoulder of said body blocking rearward movement of the plastic insert relative to the body.

15. A lancet for skin pricking, comprising:

an elongate tubular plastic body, the body having a closed forward end and an open rearward end, and an interior first tubular region; and a plastic insert, the insert being a monolithic structure comprising a second tubular region and a closed forward end providing an integral sharp tip, the insert being located within the body with an outer surface of the insert contacting an inner surface of the body, blocking forward movement of the insert relative to the body, and an outer surface of the insert contacting an interior shoulder of the body, blocking rearward movement of the insert relative to the body, the insert thus being immovable relative to the body, with the integral sharp tip projecting through said forward end of the body, and with the first tubular region and the second tubular region together defining a tubular passage closed at said forward end and open at said rearward end.

16. A lancet for skin pricking, comprising:

an elongate tubular plastic body of a first plastic material, the body having a forward end and a rearward end, and an interior surface defining a first tubular region; and a plastic insert consisting of a second plastic material comprising liquid crystal polymer, the second plastic material being different from the first plastic material, the insert being a monolithic structure comprising: a second tubular region, a closed forward end, and an integral sharp tip, the first tubular region of the body and the second tubular region of the insert together defining a tubular passage closed at the forward end, the lancet being formed by a molding process comprising first molding the insert as a monolithic structure and then molding the body over the insert, the molding process being such that the forward end of the body is closed by an end wall, the sharp tip projecting through a forward surface of the end wall and a rear surface of the end wall abutting the closed forward end of the insert, blocking forward movement of the insert relative to the body, and being such that the body forms an interior shoulder within the first tubular region and abutting the cylindrical rear portion of the insert, blocking rearward movement of the insert relative to the body, thereby permanently affixing the insert relative to the body.

* * * * *